United States Patent
Bar et al.

(10) Patent No.: US 6,916,911 B1
(45) Date of Patent: Jul. 12, 2005

(54) USE OF FIBRINOGEN MULTIMERS

(75) Inventors: Lily Bar, Rehovot (IL); Israel Nur, Rehovot (IL)

(73) Assignee: OMRIX Biopharmaceuticals SA, Rhode-St-Genese (BE)

( * ) Notice: Subject to any disclaimer, the term of this patent is extended or adjusted under 35 U.S.C. 154(b) by 215 days.

(21) Appl. No.: 09/744,973

(22) PCT Filed: Aug. 11, 2000

(86) PCT No.: PCT/EP00/07843
§ 371 (c)(1),
(2), (4) Date: Apr. 16, 2001

(87) PCT Pub. No.: WO01/12244
PCT Pub. Date: Feb. 22, 2001

(30) Foreign Application Priority Data

Aug. 13, 1999  (EP) ............................................ 99115958

(51) Int. Cl.[7] ............................ C07K 1/14; C07K 14/75
(52) U.S. Cl. ...................... 530/380; 530/382; 530/412; 530/414; 514/2
(58) Field of Search .............................. 530/380, 382, 530/412, 414; 514/2

(56) References Cited

U.S. PATENT DOCUMENTS

| 4,362,567 A | 12/1982 | Schwarz et al. |
| 4,650,678 A | 3/1987 | Fuhge et al. |
| 4,960,757 A | 10/1990 | Kumpe et al. |

FOREIGN PATENT DOCUMENTS

| EP | 0 856 317 A1 | 8/1998 |
| WO | WO9422503 | * 10/1974 |
| WO | WO9833533 | * 8/1998 |

OTHER PUBLICATIONS

Reis et al. Recovery of Fibrinogen in Cryoprecipitate Pasteurized in the Presence of Sucrose and Glycine. Brazilian J. Med. Biol. Res. vol. 26, pp. 473–476 (1993).*

* cited by examiner

*Primary Examiner*—Brenda Brumback
*Assistant Examiner*—Anish Gupta
(74) *Attorney, Agent, or Firm*—Jacobson Holman PLLC

(57) ABSTRACT

Use of fibrinogen multimers having at least 6 fibrinogen units as an ingredient for a fibrin sealant.

7 Claims, 5 Drawing Sheets

USE OF FIBRINOGEN MULTIMERS

Figure 1:
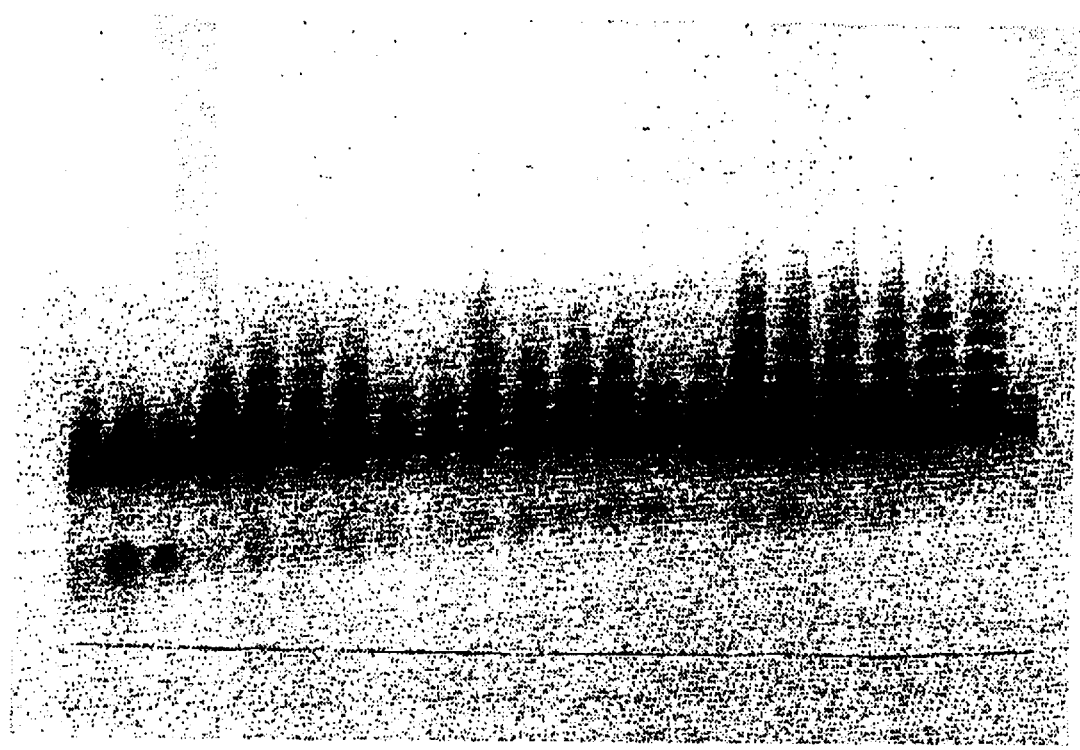

The invention is concerned with the use of fibrinogen multimers as an ingredient of a fibrin sealant and a method of producing a fibrin sealant comprising multimers.

Fibrin sealant is a generic name covering a complex of plasma derivatives which are usually composed of proteins, which mimic those active in the last stage of the coagulation cascade, from the activation of soluble fibrinogen by thrombin to the formation of insoluble protein fibrin (Matras 1985, Sierra 1993, Spotnitz et al 1987 and Spotnitz 1995). Most of the commercial fibrin sealants are composed of two major components—thrombin supplemented with $Ca^{++}$ ions and fibrinogen supplemented with varying amounts of factor XIII. Once both components are mixed, the thrombin splits off fibrinopeptides A and B from the respective Aa and Bb chains of fibrinogen to form fibrin monomers that are polymerized by hydrogen bonding to form a soluble fibrin clot. Factor XIII, activated by thrombin in the presence of $Ca^{++}$ ions, catalyzes crosslinking between the fibrin molecules, increasing the mechanical strength of the clot and reducing its susceptibility to proteolytic cleavage (Gladner and Nossal 1983).

Most fibrin sealants are prepared from either plasma cryoprecipitate or from Cohn fraction I, as sources of fibrinogen. Cryoprecipitate is obtained by thawing frozen plasma at 2–4° C., resulting in a paste that is recovered by centrifugation. Cryoprecipitate contains fibrinogen, fibronectin, vonWillebrand factor and other proteins that are co-precipitated with the above proteins, such as albumin, IgG, IgM, IgA, vitamin K-dependent-clotting factors and factor XIII (FXIII). Since the use of plasma cryoprecipitate, as a source for the sealant, may result in a lower activity of factor FXIII (Radosevich et al, 1997) some of the companies add exogenous factor XIII from various sources. Products manufactured from cryoprecipitate such as TissuCol (which has recently received a free marketing authorization in the US) and BeriPlast have been in the European market for more than a decade, however FXIII is not added to any of these products in the U.S. Cohn fraction I, or equivalent products, are prepared by ethanol precipitation of plasma by 8–10% ethanol at −30° C.–−50° C. at neutral pH. BioCol™ produced by Plasma Product services, Lille France is such product. The product is manufactured by processing the whole plasma. Prior to a 10% cold ethanol precipitation, the plasma is thawed at 37° C. for at least 6 hours followed by recovery of the fibrinogen by centrifugation. The paste is then reconstituted in Tris/lysine buffer and subjected to a second 10% cold ethanol precipitation for an additional 10–12 hours. This allows for highly purified fibrinogen, which is then treated by solvent detergent for virus inactivation. The final product is lyophilized for prolonged storage at 4° C. (Burnouf-Radosevich et al 1990).

Fibrinogen integrity and structure are of most importance for the performance of fibrin sealant. The rates of polymerization, binding to the fibrin receptor and susceptibility to fibrinolytic digestion have a critical influence on the performance in the clinical arena.

Fibrinogen, a tri-domainal (two D domains and a central E domain) disulfide bond molecule about 47 nm in length, is composed of two symmetrical half-molecules, each consisting of a set of three different polypeptide chains terms Aa, Bb and γ. The halves are covalently joined in the central amino-terminal E domain by five disulfide bridges. Reciprocal disulfide bridges are formed between the γ8 and γ9 position, thus orienting the γ chains in an anti-parallel direction (Mosesson, 1997). Removal of the fibrinopepties A and B upon activation by thrombin induces a spontaneous polymerization of the fibrin monomer molecule via noncovalentic binding.

Although fibrinogen has insufficient centers for such polymerization, nevertheless, in suitable conditions and without any enzymatic action, such as at high fibrinogen concentration, low ionic strength, or long incubation at 4° C., fibrinogen is polymerized (Rozenfeld and Vasileva 1991). Fibrinogen is liable to undergo self-association according to some authors to form structures that are either similar to fibrin (Cohen et al 1966; Gollwitzer et al 1983; Ugarova et al 1987) or to quasi-globular particles (Becker 1987).

Rozenfeld and Vasileva (1991) found that the molecules of fibrinogen undergo a spontaneous modification of their carboxyl terminals and bind end to end into flexible polymer chains. On attaining a critical length, the single-filament polymers twist into a coil and aggregate to form branch molecules in which the segments are packed sufficiently densely to resemble strong hydrated globular particles. The formation, under the influence of factor XIIIa, of ε/γ-glutamyl-lysine covalent bonds produced only insignificant changes in the spatial organization of the fibrinogen aggregates. Covalent dimerization of the γ-chains restricts the structural flexibility of polymers, but linking of the a-chains provides progressive compaction of the structure with an increase in its molecular weight. Electrophoresis of reconstituted samples shows that the coil-shaped chains of fibrinogen oligomers prevent the complete enzymatic linking of the γ-chains. From the results of their work, the authors suggest that the accelerated assembly of multimolecular aggregates, seen in the presence of Factor XIIIa, may be explained by the stabilization of intermediate complexes of fibrinogen, which make the spontaneous transition from a stable native state to the active state irreversibly. However a more recent paper by Mosesson claims that fibrinogen molecules become covalently crosslinked by factor XIIIa in the same sequence as in fibrin, i.e. first the a and then the γ chain (Mega et al 1988, and Mosesson et al 1995).

It is an object of the present invention to provide a fibrin sealant having improved properties.

According to the invention fibrinogen multimers having at least 6 fibrinogen units are used as an ingredient of a fibrin sealant. Preferably, 6–15 fibrinogen units in the multimer are used. Still more preferred are 6–9 fibrinogen units. In particular 8 or 9 units are present in the multimer.

A method for manufacturing the fibrin sealant having fibrinogen multimers with at least 6 units comprises the steps of resuspending cryoprecipitate adding sucrose to yield a concentration of 60 to 70% (w/w), adding glycine to yield a concentration of 0.1 to 0.3 M, heating to 60° C. for 15–20 hours, removing the glycine and the sucrose by dialysis, adding a protease inhibitor.

Preferably, the dialysis is conducted against a buffer comprising NaCl, glycine and $CaCl_2$.

Typically, the protease inhibitor is tranexamic acid in a concentration of 8–12% (w/w) and/or arginine in a concentration of 1–3% (w/w).

Subject of the present invention is also a fibrin sealant comprising multimeric fibrinogen having at least 6 fibrinogen units.

In order to investigate the influence of the nature of the fibrinogen component in fibrin sealants, the immunoreaction of the non-reduced agarose SDS electrophoresis method was modified first established by Connaghan et al (1985) and by Proietti et al (1990). The modification of this semi-quantitative method initially designed to monitor fibrin crosslinked polymers and its degradation products in plasma, was used for monitoring the number of fibrinogen monomers/units and their amounts in each oligomer in various fibrinogen preparations and in fibrin sealants.

Even though a detailed protocol for fibrinogen identification using agarose horizontal gel electrophoresis has been published in 1990, the method was unsatisfactory for the separation of high molecular wt. fibrinogen protein (Proietti et al 1990). The method developed by Reines (1990) for the detection of vWF multimers to be used for the immunodetection of fibrinogen, was modified as follows: The Horizontal Electrophoresis was performed using the Reines et al (1990) detailed protocol for vWF multimers, however, the detection of fibrinogen multimers and the analysis method were of Proietti et al (1990), with some modifications (Proietti et al 1990). Briefly, samples were prepared by diluting to a protein concentration of 0.1 mg/ml in a solution of 70 mM Tris, 4 mM EDTA, 2.4% SDS, 9 M urea and 0.1 g/L bromophenol blue added as a marker and incubated at 60° C. for 30 min. Agarose was dissolved to a final concentration of 1% (stacking gel), 1.6% (cathode gel) and 2% (separating gel) by boiling in 70 mM Tris, 4 mM EDTA and 4% SDS (stacking gel buffer) or 100 mM Tris, 150 mM glycine and 0.1% SDS (cathode gel buffer and cathode buffer) or 200 mM Tris, 100 mM glycine and 0.4% SDS (separating gel buffer). Gels (cathode, stacking and separating gels) were cast at >50° C. and allowed to polymerize for at least 2 hours for each gel. Samples were loaded at 0.6–0.9 µl per well, then electrophoresis was performed toward the anode at 600–650 volts/running hours at a constant temperature of 16° C. on a flat bed electrophoresis apparatus (Pharmacia Fine Chemicals, Sweden). The running buffer was connected to the gel via 4–8 layers of filter paper immersed in electrode buffer (the anode buffer had half the strength of the cathode buffer). Electrophoresis proceeded until the tracking dye had migrated a distance of 6–8 cm. After electrophoresis, the gel was removed, the stacking and cathode gels taken away and the separating gel washed in transfer buffer (25 mM Tris-HCl, 192 mM glycine pH 8.3 buffer, diluted 1:2 in 20% methanol) for approximately 1 minute.

Immunoblotting was performed onto a Nitrocellulose membrane (Optiran BA-S83 S&S Germany), cut to size, using the capillary blotting procedure (Reines et al 1990). After protein transfer, the nitrocellulose membrane was carefully removed from the capillary blotting unit and the residual protein binding capacity blocked by immersion in blocking buffer (0.5% I-Block Tropix, USA, 0.05% Sodium Azide in PBS) for 1 hour. Immunodetection of fibrinogen multimers was done using a goat polyclonal anti-human fibrinogen antibody (Sigma, USA), and a rabbit polyclonal anti-goat immunoglobulin alkaline phosphatase conjugate (Sigma, Mo USA) was used for immunostaining.

SDS-Polyacrylamide electrophoresis was done in a vertical electrophoretic unit (Hoefer Scientific Instruments, San Francisco, Calif. USA) using a reducing system containing 250 mM Tris, 40% glycerol, 4% SDS and 4% β-Mercaptoethanol (loading buffer). The separating gel was prepared as a gradient from 6 to 12% acrylamide concentration (from a 30% acrylamide and 0.8% bisacrylamide stock solution) containing 10% ammonium persulfate and 0.02% TEMED. The samples were mixed with 4× loading buffer to ¼ of the final volume and heated in a dry block at 95° C. for 5 minutes. The gel was run at 200V and the electrophoresis was stopped when the Bromophenol Blue reached the bottom of the gel. Immunodetection was performed using a semi-dry immuno-blotter (Hoefer Scientific Instruments, San Francisco, Calif. USA) onto a nitrocellulose membrane using the same antibodies and protocol as for the horizontal electrophoresis.

FIG. 1 shows the immunodetection of fibrinogen multimers of three plasma fractionations in-process sources of fibrinogen. One source derived from Paste I was supplemented with Factor FXIIIa. (From right to left) Lanes 1–6: cryoprecipitate; Lanes 7–12: purified fibrinogen; Lanes 13–18: purified Fibrinogen+FXIIIa; Lanes 19–21: solvent detergent paste I; Samples were taken during the process of the invention; Lanes 1, 7, 13 and 19: samples taken at the beginning of the process. Lanes 2, 8, 14 and 20: samples taken after the addition of sucrose and glycine. Lanes 3, 4, 9, 10, 15, 16 and 21: taken after incubation at 60° C. for 17 hours. Lanes 5, 11, and 17: taken after dialysis and ultrafiltration. Lanes 6, 12, 18, and 22: taken after the formulation with 10% Tranexamic acid and 2% Argenine. All the samples were loaded at 0.7–0.9 µg per lane.

Figure 2:
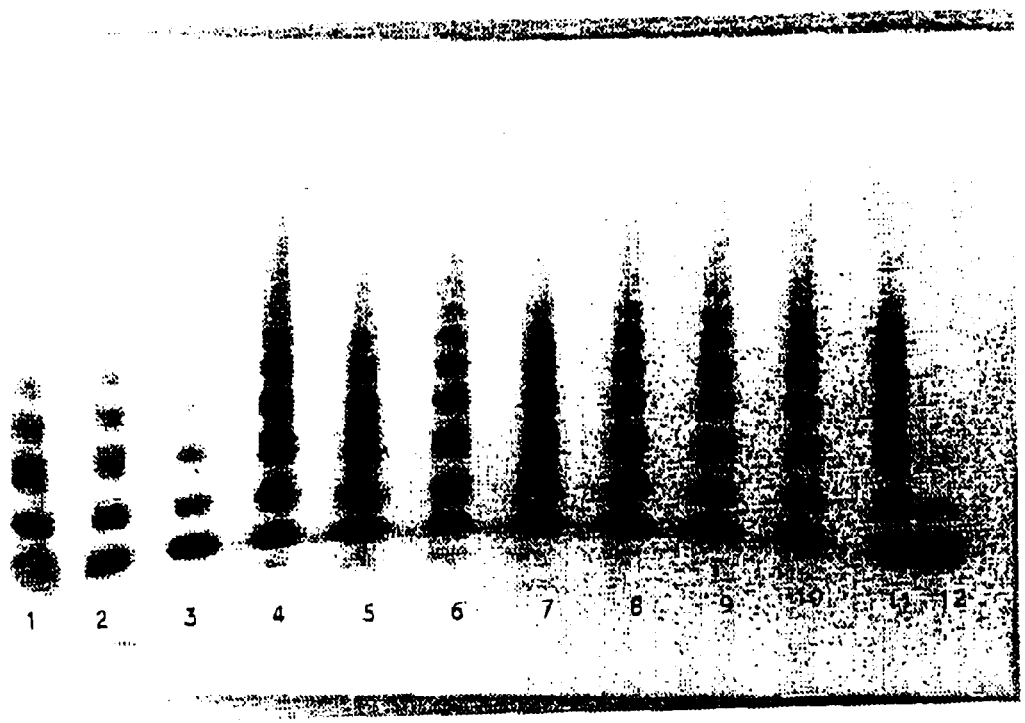

FIG. 2 shows the immunodetection of fibrinogen multimers electrophoresed on agarose SDS gel. Fibrinogen samples are of eight batches of the product of the present invention—lane 4: #C31102; lane 5: C30092; lane 6: C29081; lane 7: C27071; lane 8: C25061; lane 9: C22052; lane 10: 14032; lane 11: C12022. Four additional commercial sources of fibrinogen were added—lane 1: Tisseel™; lane 2: BeriPlast; lane 3: BioCol and lane 12: fibrinogen from Enzyme Research Inc. All the samples were loaded at 0.65 µg per lane.

Figure 3:
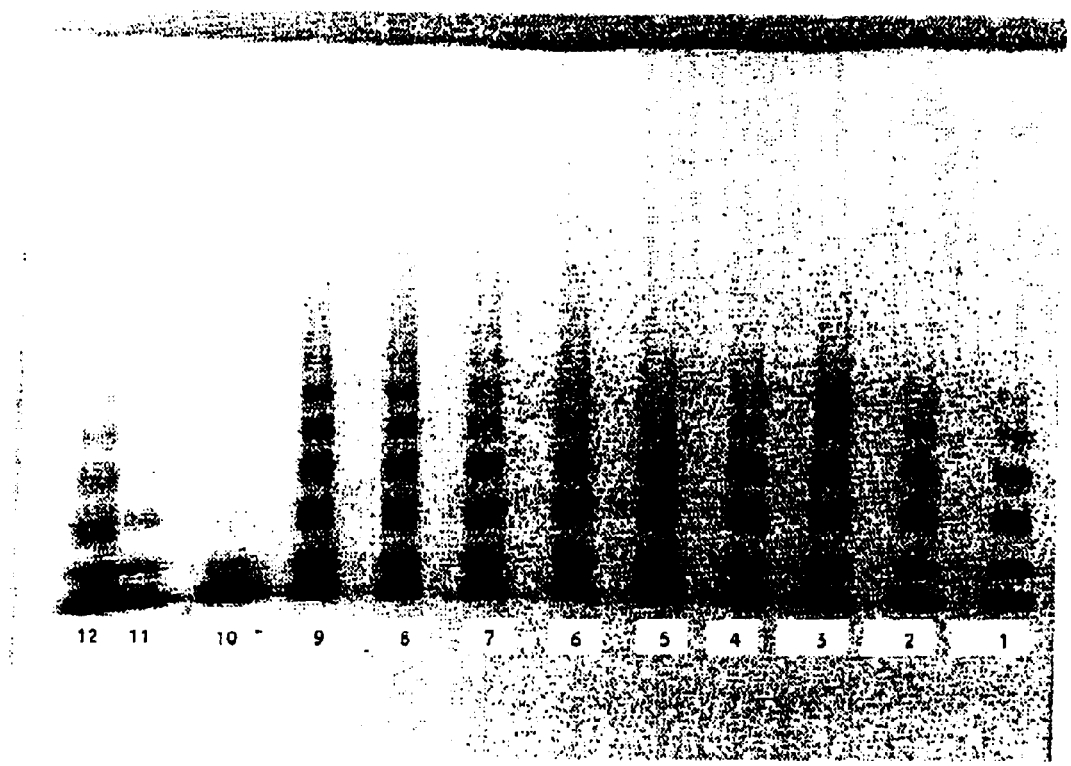

FIG. 3 shows the immunodetection of fibrinogen multimers of three commercial preparations of fibrin sealants: From left to right. Lane 12: Tisseel™; lane 11: BioCol; lane 10: Fibrinogen from Enzyme research Inc.; lane 9: product prepared according to the method of the invention. Other lanes are fibrinogen production in process samples taken after the following steps: lane 1: cryoprecipitate resuspension sample-BC01; lane 2: aluminum alhydrogel absorption sample-BC02; lane 3: SD treatment-BC04; lane 4: SD removal-BC06; lane 5: after pasteurization-BC09; lane 6: addition of stabilizers-BC10; lane 7: final concentration-BC11, lane 8: sterile bulk-BC12. All the samples were loaded at 0.65 µg per lane.

Figure 4:
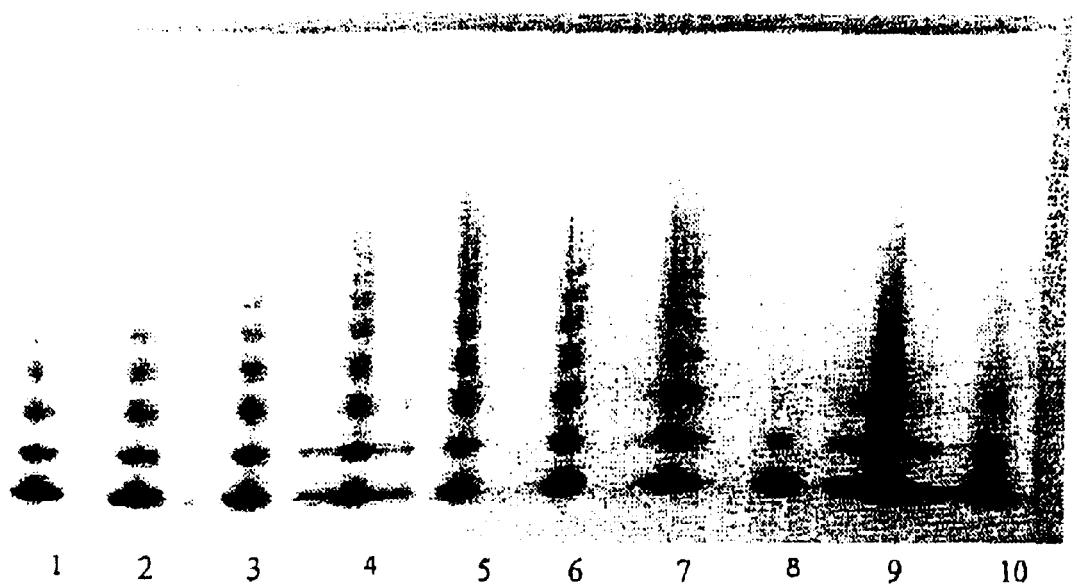

FIG. 4 shows a western blot-immunodetection of various formulations of urea non-reduced fibrinogen multimers of product prepared according to the method of the invention, run by Agarose-SDS gel electrophoresis. Lane 1: no Arginine and no Tranexamic acid; lane 2: 2% Arginine; lane 3: 2% Arginine and 5% Tranexamic acid; lane 4: 2% Arginine and 10% Tranexamic acid; lane 5: 10% Tranexamic acid, lane 6: 1% Arginine and 10% Tranexamic acid; lane 7: 4% Arginine and 10% Tranexamic acid, lane 8: Fibrinogen from Enzyme Research Inc.; lane 9: Tisseel™; lane 10: BioCol. All samples were loaded at 0.65 µg protein per lane.

Figure 5:
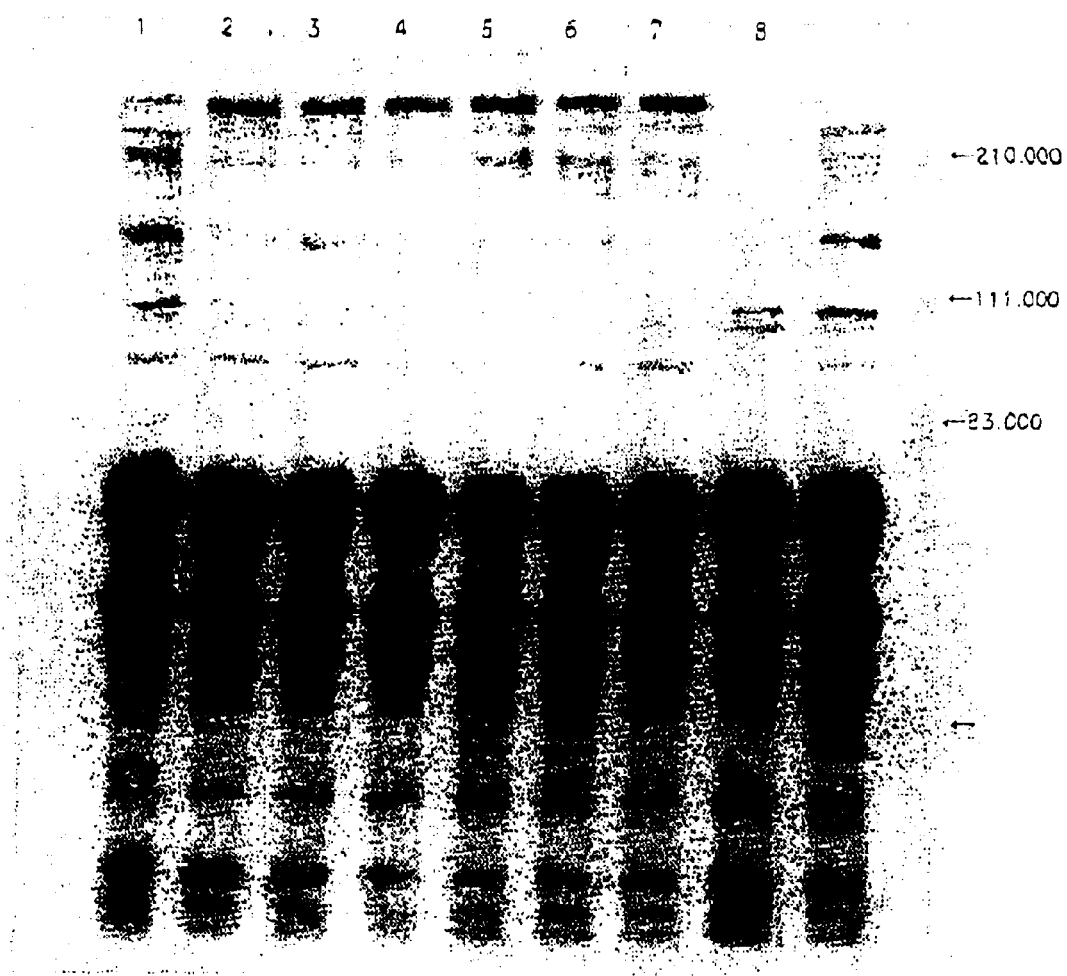

FIG. 5 shows western blot-immunodetection of various formulations of reduced fibrinogen multimers of product prepared according to the method of the invention, migrated on PAGE-SDS gel electrophoresis. Lane 1: No Arginine and no Tranexamic acid; lane 2: 2% Arginine; lane 3: 2% Arginine and 5% Tranexamic acid; lane 4: 2% Arginine and 10% Tranexamic acid; lane 5: 10% Tranexamic acid; lane 6: 1% Arginine and 10% Tranexamic acid; lane 7: 4% Arginine and 10% Tranexamic acid, lane 8: Fibrinogen from Enzyme Research Inc.; lane 9: Tisseel™. All samples were loaded at 10 µg protein per lane.

The initial fibrinogen multimeric state in various fibrinogen sources and the effect of a production process on the polymerization was identified. Three fibrinogen sources were used: 1) Re-suspension of cryoprecipitate (Sample A, Omrix Biopharmaceuticals LTD (Israel); 2) purified fibrinogen, derived from Cohn Fraction I (Sample B, Enzyme Research, USA) or purified fibrinogen supplemented with FXIIIa (Sample C, Enzyme Research USA) and 3) solvent detergent treated fraction I (Sample D, from OctaPharma (Austria). They were treated with the process of the present invention. Pasteurization, dialysis and formulation with Tranexamic acid and Arginine and at each stage of the procedure, samples have been taken to test the state of polymerization (see Table 1).

Samples labeled A4, B4 and C4 are re-suspended fibrinogen samples mixed with sucrose and glycine, incubated at 37° C. for less than 4 hours. Then, incubation at 60° C. for 17 hours was performed and dialyzed against 10 mM citrate buffer 120 mM NaCl, 120 mM glycine and 1 mM $CaCl_2$ (lanes 4, 10 and 16 in FIG. 1).

Samples labeled A5, B5, C5 and D5 are re-suspended fibrinogen samples mixed with sucrose and glycine, incubated at 37° C. for less than 4 hours, incubated at 60° C. for 17 hours, and dialyzed against 10 mM citrate buffer 120 mM NaCl, 120 mM glycine and 1 mM $CaCl_2$. The resulting solution was then formulated with 10% Tranexamic acid and 2% Arginine (lanes 5, 11 and 17 in FIG. 1). For additional clarifications see Table 1.

TABLE 1

Experimental design of fibrinogen treatments, sources, addition of Factor XIIIa, incubation at high temperature, formulation during the pasteurization with sucrose and glycine and addition of final product stabilizers, Tranexamic acid and Arginine. The effect of all these parameters on the fibrinogen multimeric state was tested.

| Lane # | No. of sample | Name of sample | Procedure - end point of treatment | Incubation temperature | Incubation time at the last point |
|---|---|---|---|---|---|
| 1 | A1 | Cryoprecipitate | — | — | 0 |
| 2 | A2 | Cryoprecipitate | Sucrose, glycine | 37° C. | 4 h |
| 3 | A3 | Cryoprecipitate | pasteurization | 60° C. | 17 h |
| 4 | A3' | | | | |
| 5 | A4 | Cryoprecipitate | dialysis and ultrafiltration | RT | 3 h + 2.5 h |
| 6 | A5 | Cryoprecipitate | add 10% TEA, 2% Arginine | RT | 1 h |
| 7 | B1 | Purified Fibrinogen | | RT | 0 |
| 8 | B2 | Purified Fibrinogen | Sucrose, glycine | 37° C. | 2 h |
| 9 | B3 | Purified Fibrinogen | pasteurization | 60° C. | 17 h |
| 10 | B3' | | | | |
| 11 | B4 | Purified Fibrinogen | dialysis and ultrafiltration | RT | 3 h + 2.5 h |
| 12 | B5 | Purified Fibrinogen | add 10% TEA, 2% Arginine | RT | 1 h |
| 13 | C1 | Purified Fibrinogen + FXIII | | RT | 0 |
| 14 | C2 | Purified Fibrinogen + FXIII | Sucrose, glycine | 37° C. | 2 h |
| 15 | C3 | Purified Fibrinogen + FXIII | pasteurization | 60° C. | 17 h |
| 16 | C3' | | | | |
| 17 | C4 | Purified Fibrinogen + FXIII | dialysis and ultrafiltration | RT | 3 h + 2.5 h |
| 18 | C5 | Purified Fibrinogen FXIII | add 10% TEA, 2% Arginine | RT | 1 h |
| 19 | D1 | Fraction I S/D | | RT | 0 |
| 20 | D2 | Fraction I S/D | Sucrose, glycine | 37° C. | 1.5 h |
| 21 | D3 | Fraction I S/D | pasteurization | 60° C. | 17 h |

Samples labeled A1, B1, C1 and D1 are re-suspended fibrinogen samples that have been directly taken for testing (lanes 1, 7, 13 and 19 in FIG. 1).

Samples labeled A2, B2, C2 and D2 are re-suspended fibrinogen samples mixed with 65% (w/w) sucrose and 0.2 M glycine, incubated at 37° C. for less than 4 hours, heated to 60° C. to allow for complete sucrose dissolution (lanes 2, 8, 14 and 20 in FIG. 1).

Samples labeled A3, B3, C3 and D3 are re-suspended fibrinogen samples mixed with sucrose and glycine, incubated at 37° C. for less than 4 hours and incubated at 60° C. for 17 hours (lanes 3, 9, 15 and 21 in FIG. 1).

FIG. 1 shows that the cryo-precipitate fibrinogen source has more fibrinogen multimers than the other fibrinogen sources, as it can be seen in bands 1, 7, 13 and 19. On the other hand, the 60° C. incubation increased the number and the amounts of fibrinogen units per multimer and the percentage of multimeric fibrinogen. However, this effect is most evident in purified fibrinogen and in Fraction I (lanes 9 and 15). The effect of FXIIIa addition is marginal, probably since all fibrinogen sources from plasma contain traces of FXIII.

The effect of fibrinogen source is further demonstrated in FIG. 2. FIG. 2 shows multimers of fibrinogen of fibrin sealant produced using the process of the invention, from cryoprecipitate after double virus inactivation (solvent detergent and pasteurization) and stabilizer addition from eight batches. FIG. 2 also presents the Multimeric State of four fibrinogen concentrates from commercial sources (Purified fibrinogen Enzyme Research, TissuCol, Biocol and Beriplast). As can be noted from the figure, purified fibrinogen (Enzyme research Inc.) derived from Fraction I is primarily a monomer. However that preparation contains a small amount of fibrinogen dimeric structure. On the other hand, commercial fibrinogen products, which compose part of fibrin sealants, contain fibrinogen multimers up to pentamers while the fibrin sealant of the present invention has high multimeric fibrinogen structures reaching up to octamers or nanomers. Furthermore, the batch to batch reproducibility, relative to the high multimeric state of fibrinogen, is evident.

The first part of the study revealed that pasteurization has a major effect on the polymerization of fibrinogen from Fraction I. However, the effect on cryoprecipitate was not fully demonstrated. In the second part of the study, the changes in the Multimeric State of fibrinogen during the production process and the batch to batch variability were examined. Samples were withdrawn from the process and the material was subjected to examination by immunodetection after agarose gel electrophoresis. FIG. 3 shows fibrinogen immunodetection of samples obtained following each production step: cryo-resuspension—lane 1; alhydrogel absorption lane 2; SD treatment—lane 3, SD removal—lane 4, post-pasteurization—lane 5, stabilizer addition—lane 6, final concentration—lane 7, sterile bulk—lane 8 and final container—lane 9, purified fibrinogen—lane 10 and the two commercial fibrinogen concentrates (Tissel and Biocol)—lanes 11 and 12 respectively. The figure clearly shows that even though the cryo-resuspension contains six-mers (lane 1), the addition of stabilizers (lane 6) promoted fibrinogen polymer formation since lane 6, sample after stabilizers addition, contains at least one more multimeric unit than the previous sample, after pasteurization (line 5). This clearly indicates that the addition of Arginine and Tranexamic acid had an effect on the fibrinogen multimeric state.

In order to examine the effect of each of the stabilizer, a sample was withdrawn from the process prior to stabilizer addition. At this point, several combinations of Arginine and Tranexamic acid were formulated containing between 0–4% and 0–10% (w/w) respectively. The different formulations were frozen, stored for seven days and thawed at 37° C. After thawing, the samples, together with purified fibrinogen and commercial fibrin concentrates, were run on a horizontal SDS-Agarose non reduced and vertical reduced β-mercaptoethanol SDS-PAGE) electrophoresis. The results are shown in FIGS. 4 (horizontal SDS-Agarose non-reduced) and 5 (SDS-PAGE reduced β-mercaptoethanol SDS-PAGE). The horizontal agarose gel electrophoresis followed by specific immunodetection of fibrinogen shows that addition of Arginine promotes multimer formation but the main contribution to its effect is done by the addition of Tranexamic acid. This finding is supported by samples that contains 0% Arginine and 10% TEA which produced more and larger fibrinogen multimers than 2% Arginine and 0% TEA. The same phenomenon can be seen on the reduced β-mercaptoethanol SDS-PAGE conducted on the same samples (FIG. 5). A new band with a molecular weight above 250 kD appears in all formulations but not in the formulation with no stabilizers and not in the commercial concentrated fibrinogen tested (fibrinogen form Enzyme Research Inc and Tisseel™). Furthermore, in the samples formulated with 10% Tranexamic acid, this high molecular weight band is much more intense than other formulations, indicating an increase in the ratio of a high number of multimeric units. Another observation that can be made from the figure is the absence of almost all the γ—γ and a-γ fibrinogen dimers from samples produced according to the method of the invention that are quite abundant in other fibrinogen concentrates (Siebenlist and Mossesson, 1996). This suggests that the increase of fibrinogen polymers is at the expense of fibrinogen dimers. Moreover, the addition of Tranexamic acid and Arginine might stabilize the fibrinogen polymers or even drive the reaction towards a higher multimeric state.

It was established that native fibrinogen, left undisturbed, forms reversible temperature-dependent aggregates (Becker and Waugh, 1980; Becker, 1987). Based on light scattering and viscosity examinations Rozemfeld and Vasileva, (1991) suggested that fibrinogen undergoes spontaneous self-association through its D domain to form flexible end to end polymer chains. They found that self-association accrued more rapidly when factor XIIIa was present, but the spatial arrangement of the fibrinogen molecules remained the same. Masesson and Siebenlist 1995 supply direct ultra-structural evidence for such associations (Siebenlist and Mossesson, 1996). However, the extent of these polymers has never been investigated in highly concentrated fibrinogen of the commercial available fibrin sealants. Furthermore in this manuscript, for the first time, evidence is been given for a fractionation production process which might lead to such high multimeric appearance of fibrinogen.

As noted in FIGS. 1 and 3, Cryoprecipitate production resulted in a high multimeric structure. However, during the production process, some of the highest molecular multimers (seven to nine fibrinogen units) are lost, probably due to filtration and precipitation. Later steps in the process of the invention, such as pasteurization and stabilization with negatively charged amino acid, recovered the high multimeric state and stabilized it even during a prolonged storage (see FIG. 2). Other commercial product such as BeriPlast™ and Tisseel™ also derived from cryoprecipitate, however, the final product contains lower multimeric fibrinogen. Both contain 4–5 fibrinogen units whereas the product prepared according to the process of the invention contains about 8–9 fibrinogen units. A different manufacturing process and different formulation may explain this difference. Both are formulated with Aprotinin and a low concentration of amino acid whereas the fibrin sealant prepared according to the process of the invention is formulated with a high concentration of Tranexamic acid and Arginine. This high salt concentration probably facilitated the formation of the high molecular wt. multimers. BioCol on the other hand is produced from a modification of Cohn fraction I. This starting material has a low multimeric state (see FIG. 1), probably because of the presence of a high concentration of ethanol which suppresses the enzymatic activity of FXIII during the precipitation of fibrinogen.

The clinical relevance of the multimeric state has to be assessed carefully by conducting well designed animal experiments. Since such experiments involve strong commercial interest, these experiments have to be performed in a well-controlled manner. The animal model consists of spraying of adhesive/fibrin sealant to control bleeding caused by partial liver resection in heparinized rabbit. Results show that the bleeding time and the amount of glue used were significantly shorter and lower for the fibrin sealant prepared according to the process of the present invention than in other fibrinogen concentrate tested (BeriPlast™ and Tisseel™). These outcomes may indicate that it has better adhesive properties to tissue than other glues. There are also reports indicating that it seems to work also at low temperature in indications such as liver transplantation. One explanation of the high adherence to tissue may be related to the high multimeric state of it as compared to the other fibrin sealants tested. These large molecules, some of them of more than $2 \times 10^6$ D molecular wt, are structurally very similar to the fibrin network. These protein macromolecules have better adhesive forces than their monomeric units, very similar to the phenomenon known in vWF Multimers.

REFERENCES

1. Becker, C. M. (1987) Bovine fibrinogen aggregates: Electron microscopic observations of quasi-globular structures, *Thromb. Res.* 48, 101–110.
2. Becker, C. M., and Waugh, D. F. (1980) Bovine fibrinogens: Reversible polymer formation, *Arch. Biochem. Biophys.* 204, 101–108.
3. Burnouf-Radosevich M, Burnouf T, Huart J J: Biochemical and physical properties of solvent-detergent-treated fibrin sealant. Vox Sang 1990; 58:77–84.
4. Cohen G, Stayer H, Kucera J Hall C, 1966 Polymorphism in fibrinogen aggregates J Mol Biol 22: 385–388.
5. Connaghan D G, Francis C W, Lane D A, Marder V J. Specific identification of fibrin polymers, fibrinogen degradation products, and crosslinked fibrin degradation products in plasma and serum with a new sensitive technique. Blood 1985; 65:589–97
6. Gladner J A, Nossal R. Effects of crosslinking on the rigidity and proteolytic susceptibility of human fibrin clots Thromb Res 1983, 30:273–88
7. Gollwitzer R, Bode W, Karges H E. On the aggregation of fibrinogen molecules, Thromb Res Suppl 1983; 5:41–53
8. Matras H: Fibrin seal: The state of the art. J. OrallMaxillofac Surg 1985; 43:605–611.
9. Mega, J. I., Shainoff, J. R., and Dreshar, D. A. (1988) Dissociation of α-fibrin at elevated temperatures, in Mosesson, M. W., Amrani, D. L., Siebenlist, K. R., and DiOrio, J. P. (Eds.), Fibrinogen 3. Biochemistry, Biological Functions, Gene Regulation and Expression, pp. 83–86, Elsevier/North-Holland, Amsterdam.
10. Mosesson M W. Fibrinogen and fibrin polymerization: appraisal of the binding events that accompany fibrin generation and fibrin clot assembly. Blood Coagul Fibrinolysis 1997 July; 8:257–67.
11. Mosesson, M. W., Siebenlist, K. R., DiOrio, J. P., Matsuda, M., Hainfeld, J. F., and Wall, J. S. (1995). The role of fibrinogen D domain intermolecular association sites in the polymerization of fibrin and fibrinogen Tokyo II (γ 275 arg→cys), *J. Clin. Invest.* 96, 1053–1058.
12. Proietti A B, McGuire M, Bell W. Specific identification of fibrin(ogen) degradation products in plasma and serum using blotting and peroxidase labeled antiserum. Am J. Hematol 1990; 34:270–274.
13. Radosevich M, Goubran H I, Burnouf T. Fibrin sealant: scientific rationale, production methods, properties, and current clinical use. Vox Sang 1997; 72:133–43
14. Raines G, Aumann H, Sykes S, Street A. Multimeric analysis of von Willebrand factor by molecular sieving electrophoresis in sodium dodecyl sulphate agarose gel. Thromb Res 1990; 60:201–12
15. Rosenfel'd, M. A., and Vasil'eva, M. V. (1991) Mechanisms of aggregation of fibrinogen molecules: The influence of fibrin-stabilizing factor, *Biomed. Sci.* 2, 155–161.
16. Siebenlist K R Mosesson M W. Evidence for intramolecular cross-linked Aa*γ chain heterodimers in plasma fibrinogen. Biochemistry 1996: 35:5817–5821.
17. Sierra D H: Fibrin sealant adhesive systems: A review of their chemistry, material properties and clinical applications. J. Biomater Appl 1993; 7:309–352.
18. Spotnitz W D, Mintz P D, Avery N, Bithell T C, Kaul S, Nolan S P: Fibrin sealant from stored human plasma: An inexpensive and efficient method for local blood bank preparation. Am Surg 1987; 53:460–464.
19. Spotnitz W D: Fibrin sealant in the United States: Clinical use at the University of Virginia. Thromb Haemost 1995; 74:482–485.
20. Ugarova T P, Mikhalovskaia L I, Gornitskaia O V. Aggregation of fibrinogen molecules in a solution. Ukr Biokhim Zh 1987; 59: 9–17. [Article in Russian]
21. Veklich, Y. Ang E K Loarnd, L, and Weisel J W. (1998). The complementary aggregation sites of fibrinogen investigated through examination of polymers of fibrinogen with fragment E. Proc. Natl. Acad. Sci. 1998; 95:1438–1442.

What is claimed is:

1. A method for the production of a fibrin sealant comprising fibrinogen multimers having at least 6 fibrinogen units comprising the steps of obtaining a mixture by
resuspending cryoprecipitate
adding sucrose powder to yield a sucrose/mixture concentration of 60 to 70% (w/w), and
adding glycine powder to yield a glycine/mixture concentration of 0.1 to 0.3 M, heating to 60° C. for 15–20 hours, removing the glycine and the sucrose by dialysis, and adding a protease inhibitor.

2. The method of claim 1, wherein the dialysis is conducted against a buffer comprising NaCl, glycine, and $CaCl_2$.

3. The method of claim 1, wherein the protease inhibitor is tranexamic acid in a concentration of 8–12% (w/w) and/or arginine in a concentration of 1–3% (w/w).

4. A fibrin sealant comprising multimeric fibrinogen having at least 6 fibrinogen units.

5. The fibrin sealant of claim 4, wherein 6–15 fibrinogen units are present in the multimeric fibrinogen.

6. The fibrin sealant of claim 4, wherein 6–9 fibrinogen units are present in the multimeric fibrinogen.

7. The fibrin sealant of claim 4, wherein multimeric fibrinogen having 6–9 fibrinogen units is present in an amount of at least 5% (w/w) of total fibrinogen content.

* * * * *